(12) United States Patent
Thyr et al.

(10) Patent No.: US 10,047,408 B2
(45) Date of Patent: Aug. 14, 2018

(54) ARRANGEMENT AND SYSTEM FOR A TREATMENT PROCESS

(71) Applicant: VALMET AB, Sundsvall (SE)

(72) Inventors: Anders Thyr, Sundsvall (SE); Örjan Ahlgren, Sundsvall (SE); Krister Sjöblom, Sundsvall (SE)

(73) Assignee: VALMET AB, Sundsvall (SE)

( * ) Notice: Subject to any disclaimer, the term of this patent is extended or adjusted under 35 U.S.C. 154(b) by 109 days.

(21) Appl. No.: 15/321,605

(22) PCT Filed: Jun. 24, 2015

(86) PCT No.: PCT/SE2015/050731
§ 371 (c)(1),
(2) Date: Dec. 22, 2016

(87) PCT Pub. No.: WO2015/199604
PCT Pub. Date: Dec. 30, 2015

(65) Prior Publication Data
US 2017/0175209 A1    Jun. 22, 2017

(30) Foreign Application Priority Data

Jun. 26, 2014 (SE) ...................... 1450789

(51) Int. Cl.
*C13K 1/02* (2006.01)
*C08H 8/00* (2010.01)
(Continued)

(52) U.S. Cl.
CPC ................. *C13K 1/02* (2013.01); *C08H 8/00* (2013.01); *D21C 9/02* (2013.01); *D21C 9/18* (2013.01)

(58) Field of Classification Search
None
See application file for complete search history.

(56) References Cited

U.S. PATENT DOCUMENTS 5,366,558 A    11/1994   Brink
5,411,594 A    5/1995    Brelsford
(Continued)

FOREIGN PATENT DOCUMENTS

CA    2650919 A1     7/2010
EP    0 056 263 A1   7/1982
(Continued)

OTHER PUBLICATIONS

Wingren et al., "Process Considerations and Economic Evaluation of Two-Step Steam Pretreatment for Production of Fuel Ethanol from Softwood", Biotechnology Progress, 2004, vol. 20, No. 5, pp. 1421-1429, ISSN: 8756-7938; pp. 1423, 1426-1427.

*Primary Examiner* — Melvin C. Mayes
*Assistant Examiner* — Stefanie J Cohen
(74) *Attorney, Agent, or Firm* — Birch, Stewart, Kolasch & Birch, LLP

(57) ABSTRACT

An arrangement for feeding and dewatering lignocellulosic material in a hydrolysis process between a first reactor unit, where the material is partly hydrolyzed, to a second reactor unit, wherein the first reactor unit operates at a first pressure and the second reactor unit operates at a second pressure being higher than the first pressure. The arrangement includes a first plug screw feeder arranged to receive the partly hydrolyzed material from the first reactor unit and being arranged to compress, dewater and transport the material, wherein the first screw feeder is arranged to operate at a pressure being higher than the first pressure. A dilution vessel is coupled to receive material from the first plug screw feeder and including a liquid inlet for receiving liquid to wash the material, wherein the dilution vessel is arranged to maintain or increase the pressure (PDM). A second plug screw feeder is arranged to receive the diluted material and to compress, dewater and transport the material to the second reactor unit, wherein the second screw feeder (Continued)

is arranged to operate at a pressure being higher than the pressure of the first plug screw feeder. A system including such an arrangement and a first reactor unit and a second reactor unit is also presented.

<p align="center">27 Claims, 5 Drawing Sheets</p>

(51) Int. Cl.
*D21C 9/02* (2006.01)
*D21C 9/18* (2006.01)

(56) References Cited

U.S. PATENT DOCUMENTS

| | | |
|---|---|---|
| 2009/0221814 A1 | 9/2009 | Pschorn et al. |
| 2010/0056774 A1 | 3/2010 | Anand et al. |
| 2010/0269990 A1 | 10/2010 | Dottori et al. |
| 2011/0281298 A1 | 11/2011 | Rawls et al. |
| 2013/0029406 A1 | 1/2013 | Dottori et al. |

FOREIGN PATENT DOCUMENTS

| | | | | |
|---|---|---|---|---|
| EP | 2 247 781 A2 | | 11/2010 | |
| EP | 2336344 A1 | * | 6/2011 | ............ C12M 21/12 |
| WO | WO 2009/108773 A2 | | 9/2009 | |
| WO | WO 2010/121367 A1 | | 10/2010 | |
| WO | WO 2011/039635 A2 | | 4/2011 | |
| WO | WO 2014/026154 A1 | | 2/2014 | |
| WO | WO-2014026154 A1 | * | 2/2014 | ............ C12P 19/02 |

* cited by examiner

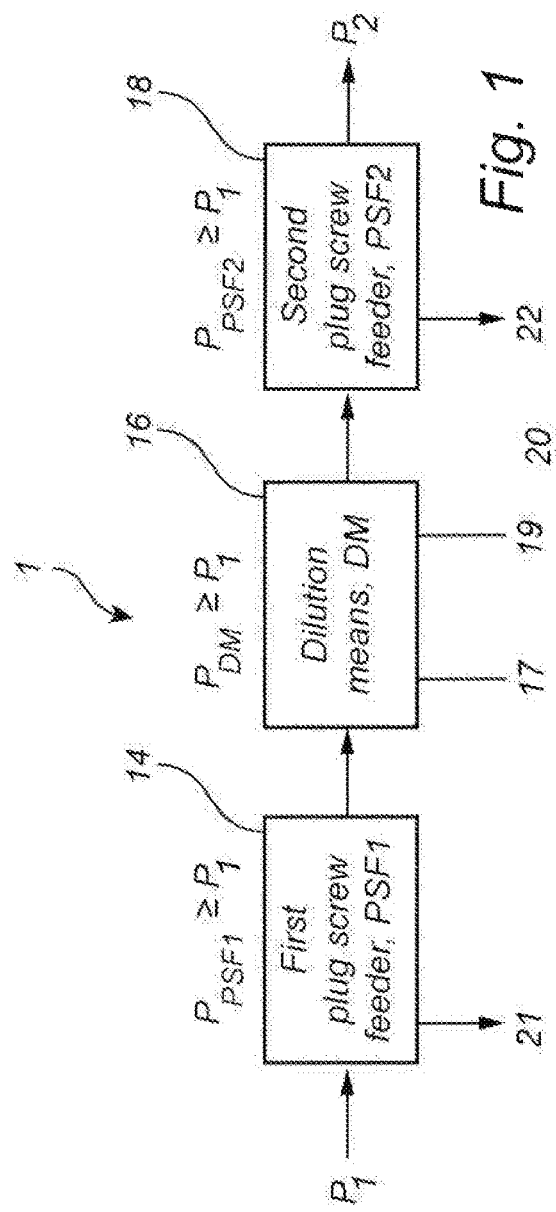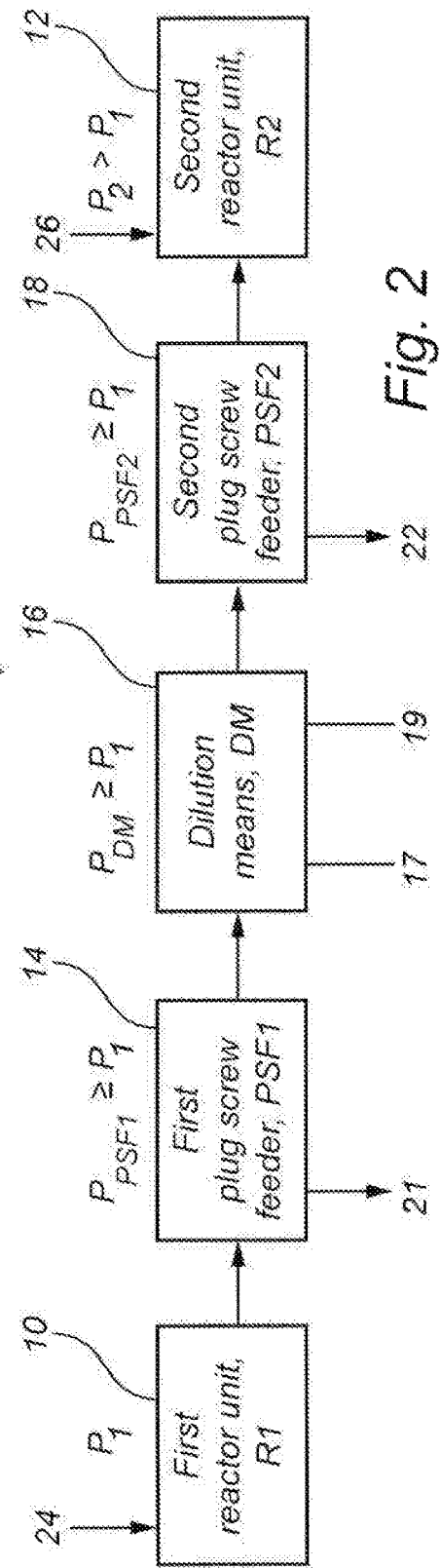

ARRANGEMENT AND SYSTEM FOR A TREATMENT PROCESS

TECHNICAL FIELD

The present invention relates to treatment of lignocellulosic material in a hydrolysis process and more specifically to arrangements for feeding and dewatering partly hydrolyzed lignocellulosic material between reactor units in a system for hydrolysis and to systems for two-stage hydrolysis of lignocellulosic material including such arrangements.

BACKGROUND OF THE INVENTION

Lignocellulosic biomass is abundant and can provide a sustainable resource for producing fuels, chemicals and biobased materials. The hemicellulose and cellulose content of the biomass can be converted to pentose and hexose sugars by acid hydrolysis with lignin as a residue. By performing the acid hydrolysis in two stages at different temperatures the total yield of sugars can be increased compared to a one-stage process. In such a process the first stage is a milder treatment targeting the hemicellulose part which is easier to hydrolyze compared to the cellulose. In the second reactor stage more severe conditions are applied to break down the cellulose into sugars. If the process would be run using one reactor unit, the liberated hemicellulose sugars would decompose further and create unwanted by-products. Hence, it is beneficial to run the hydrolysis process in two reactor units instead of one unit. Conventionally, enzymatic hydrolysis is applied after a pretreatment stage to convert lignocellulosic biomass into sugars. Such conversion processes are associated with high operating costs due to the consumption of expensive enzymes.

When the process is run in two stages a solid-liquid separation is needed between the two reactor units to remove the hemicellulose sugars prior to the second reactor unit. Conventional equipment for separation of liquid from fibrous biomass, e.g., filters and presses, operate at atmospheric pressure. This entails that the pressure has to be reduced between the two reactor units to the atmospheric pressure from the pressure of the first reactor stage in order to perform the washing and this, in turn, means that the biomass material has to be reheated to the desired temperature in the second reactor or in a pre-heating unit before entering the second reactor.

This pressure reduction and pressure increase between the reactor units is energy demanding and also time consuming. Therefore, there is a need within the biorefining industry of improved arrangements for feeding and dewatering partly hydrolyzed material between reactor units in a system for a hydrolysis process and for removing hemicellulose and hemicellulose-derived sugars from the material in the two-stage hydrolysis process.

In EP 2 247 781 a two-stage system for pre-treatment of cellulosic biomass material is presented. The pre-treatment, which includes a steam explosion stage, prepares the biomass for the following enzymatic hydrolysis stage for liberation of the sugars.

However, there is still a need in the industry for improved systems and arrangements for feeding and dewatering partly hydrolyzed material in two-stage processes.

SUMMARY OF THE INVENTION

According to an object of the present invention, there is provided an improved arrangement for feeding and dewatering at least partly hydrolyzed lignocellulosic material between reactor units in a system for a hydrolysis process.

According to another object of the present invention, there is provided an improved arrangement for removing hemicellulose from at least partly hydrolyzed material between reactor units in a two-stage hydrolysis process.

According to an object of the present invention, there is provided an improved arrangement for feeding and dewatering at least partly hydrolyzed material between reactor units in a system for a hydrolysis process at maintained high pressure or at increased pressure from the initial high pressure.

According to another object of the present invention, there is provided an improved arrangement for removing hemicellulose from at least partly hydrolyzed material between reactor units in a two-stage hydrolysis process at maintained high pressure or at increased pressure from the initial high pressure.

According to a further object of the present invention, there is provided an improved system and arrangement for feeding and dewatering at least partly hydrolyzed material in a hydrolysis process operated at high temperatures and short treatment times.

According to yet another object of the present invention, there is provided an improved system and arrangement for feeding and dewatering at least partly hydrolyzed material in a hydrolysis process operated at high pressures.

These and other objects are achieved in accordance with the appended claims.

In the context of the present invention, the term "plug screw feeder" relates to a feeder comprising a screw or similar rotating means and which is capable of feeding or transporting lignocellulosic material through the feeder at increased or maintained density of the material and that creates an essentially gas- and fluid-tight plug of the lignocellulosic material towards the end of the feeder. For example, according to an embodiment of such a plug screw feeder, a cross-sectional area of the circular housing of the feeder and the screw diameter decreases in the feeding direction thereby so as to create a decreasing space between the screw and the housing and thus resulting in an essentially gas- and fluid-tight plug of the lignocellulosic material towards the end of the feeder. According to another embodiment of a plug screw feeder, the cross-sectional area of the circular housing of the feeder is constant while and the screw diameter and screw axis increases in the feeding direction thereby creating a decreasing space between the screw and the housing and thus resulting in an essentially gas- and fluid-tight plug of the lignocellulosic material towards the end of the feeder. As the skilled person realizes, there are other embodiments of feeders that achieves this purpose and thus are included within the definition of the term "plug screw feeder".

Further, in the context of the present invention, the term "pressure lock" refers to a pressure proof barrier allowing different pressures on respective sides of the barrier.

According to an aspect of the present invention, there is provided an arrangement for feeding and dewatering lignocellulosic material in a hydrolysis process between a first reactor unit, where the material is partly hydrolyzed, and a second reactor unit, where the partly hydrolyzed material is further hydrolyzed, preferably including full hydrolysis into liberated mono sugars. The first reactor unit operates at a first pressure and the second reactor unit operates at a second pressure being higher than the first pressure. The arrangement comprises a first plug screw feeder arranged to receive the partly hydrolyzed material from the first reactor unit and being arranged to compress, dewater and transport the material, wherein the first plug screw feeder is arranged to operate at a pressure being higher than the first pressure. A dilution means is coupled to receive material from the first plug screw feeder and includes a liquid inlet for receiving wash liquid, wherein the dilution means is arranged to maintain or increase the pressure. A second plug screw feeder is arranged to receive the diluted material and is arranged to compress, dewater and transport the material to the second reactor unit, wherein the second plug screw feeder is arranged to operate at a pressure being higher than the pressure of the first plug screw feeder.

According to another aspect of the present invention, there is provided a system for a two-stage hydrolysis process comprising a first reactor unit where the lignocellulosic material is partly hydrolyzed and a second reactor unit for further processing of the partly hydrolyzed material, wherein the first reactor unit operates at a first pressure and the second reactor unit operates at a second pressure being higher than the first pressure. A first plug screw feeder is coupled to the first reactor unit and is arranged to receive the partly hydrolyzed material from the first reactor unit and compress, dewater and transport the material further, wherein the first screw feeder is arranged to operate at a pressure being higher than the first pressure. Dilution means is coupled to receive material from the first plug screw feeder and a liquid inlet is arranged to receive liquid to wash the material, wherein the dilution means is arranged to maintain or increase the pressure. A second plug screw feeder is arranged to receive the diluted material, compress, dewater and transport the material to the second reactor unit, wherein the second screw feeder is arranged to operate being higher than the pressure of the first plug screw feeder.

The present invention is based on the insight that using at least two plug screw feeders for feeding, compressing and dewatering the partly hydrolyzed biomass material between reactor units operating at different pressures can eliminate the need for lowering the temperature between the reactor units and, hence, the pressure can be increased during the transport between the reactor units. The use of the at least two plug screw feeders for transporting the partly hydrolyzed material between the reactor units also makes it possible to remove and recover dissolved hemicellulose sugars by draining of the hydrolyzate while increasing the pressure. This is possible since the plug screw feeder compresses the biomass material to form a pressure seal between an inlet and outlet of the plug screw feeder. Using at least two plug screw feeders and addition of wash liquid between a first and a second plug screw feeder makes further removal of dissolved sugars possible. It also results in a cleaner end product. This solution with at least two plug screw feeders also makes it possible to feed biomass material into reactors operating at relatively high pressure levels as the pressure can be increased in steps. Moreover, by eliminating the need for lowering the temperature between the reactor units the invention allows for a high temperature and pressure throughout the system. The present invention provides great advantages over the prior art two-stage technologies. For example, the initial pressure, e.g. the pressure of the first reactor, can be successively increased between the first and second reactor, which means that the biomass material does not need any reheating before entering a second reactor. Further, the present system and arrangement are capable of handling a high temperature process, which, in turn, allows for shorter treatment times in the reactors. Furthermore, the system according to the present invention can be operated at high temperatures and pressures and it is possible to achieve a complete hydrolysis of the biomass material into oligo and mono sugars using only the first and second reactor units. Further, the successive pressure increase in the plug screw feeder provides the additional advantages that the degree of compression of the transported material in respective plug screw feeder can be lower, for example, compared to if only one plug screw feeder had been used. A higher degree of compression results a denser pressure lock but the successive pressure increase over the two plug screw feeder enables a lower compression in respective plug screw feeder. The lower degree of compression entails a lower energy usage and also significantly reduces wear and strain on part of the plug screw such as the filter part.

The arrangement and system according to the present invention is related to treatment of lignocellulosic biomass material in a hydrolysis process and more specifically to arrangements for feeding and dewatering partly hydrolyzed biomass material between reactor units in a system for hydrolysis and to systems for two-stage hydrolysis of biomass material including such arrangements, wherein the biomass material includes, for example, wood-based raw materials such as wood chips, sawdust, chipped or hammer-milled forest residuals, agricultural residues such as bagasse, sugar cane straw, wheat straw, corn stover, corn cobs, and oil palm fruit residuals (so-called empty fruit bunches). Other types of lignocellulosic biomass material that can be used in accordance with the present invention include grasses, reeds and energy canes.

In an embodiment of the arrangement according to the present invention, the dilution means comprises a dilution vessel and may comprise a dilution screw.

According to embodiments of the present invention, the dilution means is arranged to increase the pressure from the pressure of the first plug screw feeder.

According to embodiments of the arrangement, the dilution means includes an inlet for receiving steam, wherein the received material is mixed with steam and liquid.

According to embodiments of the arrangement, the second plug screw feeder is arranged to operate at a pressure being higher than the pressure of the dilution means.

According to embodiments of the arrangement, the dilution means is arranged to increase the pressure to the second pressure.

According to embodiments of the arrangement, a plug breaking means is provided in the arrangement. In a preferred embodiment, the plug breaking means is coupled to the second plug screw feeder.

According to embodiments of the system, the dilution means is arranged to increase the pressure from the pressure of the first plug screw feeder.

According to embodiments of the system, the dilution means includes an inlet for receiving steam, wherein the received material is mixed with steam and liquid.

According to embodiments of the system, the second plug screw feeder is arranged to operate at a pressure of at least the pressure of the dilution means.

According to embodiments of the system, the first plug screw feeder is directly coupled to the first reactor unit to receive the partly hydrolyzed material and is arranged to compress and transport the material to the dilution means and the second plug screw feeder is directly coupled to the dilution means and is arranged to compress and transport the material to the second reactor unit.

According to embodiments of the system, the first reactor unit is arranged to operate at a temperature above 180° C.

According to embodiments of the system, the second reactor unit is arranged to operate at a temperature above 180° C., preferably between 180-300° C., more preferably between 225-300° C., and more preferably above 235° C.

According to embodiments of the system, the first reactor unit is arranged to operate with a treatment time below 5 minutes.

According to embodiments of the system, the second reactor unit is arranged to operate with a treatment time below 1 minute.

According to embodiments of the system, the first reactor unit is arranged to operate at a pressure within a range of 5-20 bar, preferably more than 10 bar, and more preferably within a range of 13-16 bar.

According to embodiments of the present invention, the second reactor unit is arranged to operate at a pressure within a range of 25-50 bar, preferably at least 30 bar, and more preferably within a range of 35-45 bar.

According to embodiments of the system, the first reactor unit includes a horizontal, or vertical, or inclined reactor.

According to embodiments of the system, the second reactor unit includes a horizontal, or vertical, or inclined reactor.

According to embodiments of the system, the first and second reactor comprises a conveyor screw with an adjustable rotational speed for transporting the material towards a discharge outlet at a desired rate.

According to embodiments of the system, a plug breaking means is coupled between the first and second reactor unit. In a preferred embodiment, the plug breaking means is coupled between the second plug screw feeder and the second reactor unit. Thereby, it is possible to operate the second reactor unit at high temperatures and with a short treatment times since the solid biomass material entering the second reactor unit will be broken up into small particles.

According to embodiments of the present invention, the plug breaking means comprises a rotatable plug breaking member such as rotating disc.

According to embodiments, the dilution means includes a mixing screw or a pump.

According to embodiments of the system, the biomass material has a high solid content of at least 30% (i.e. a liquid-to-solid ratio of 2.3:1) and preferably more than 50% (i.e., a liquid-to-solid ratio of 1:1) into the first reactor unit and the second reactor unit is arranged to operate with a treatment time below 1 minute.

According to embodiments of the present invention, a method for feeding and washing lignocellulosic material in a hydrolysis process between a first reactor unit where the material is partly hydrolyzed and a second reactor unit where the material is further hydrolyzed, wherein the first reactor unit operates at a first pressure and the second reactor unit operates at a second pressure being higher than the first pressure, comprises: compressing, dewatering and transporting the partly hydrolyzed material at a pressure being higher than the first pressure; diluting the material and receiving liquid to wash the material at maintained or increased pressure; and compressing, dewatering and transporting the material to further processing at a pressure being higher than the pressure of the first compressing, dewatering and transporting step.

According to a further embodiment of the present invention, a method for two-stage hydrolysis comprises: a first hydrolysis where a lignocellulosic material is partly hydrolyzed and a second hydrolysis of the partly hydrolyzed material, wherein the first hydrolysis is operated at a first pressure and the second hydrolysis operates at a second pressure being higher than the first pressure; compressing, dewatering and transporting the partly hydrolyzed material at a pressure being higher than the first pressure; diluting the material and receiving liquid to wash the material, wherein the dilution is operated at maintained or increased pressure ($P_{DM}$); and compressing, dewatering and transporting the diluted material to the second hydrolysis at a pressure being higher than the pressure of the compressing, dewatering and transporting step.

As discussed above, the present invention provides great advantages over the prior art two-stage technologies. Additional advantages of the present invention will be understood from the detailed description.

BRIEF DESCRIPTION OF THE DRAWINGS

The present invention will now be described, for exemplary purposes, in more detail by way of embodiments and with reference to the enclosed drawings, in which:

FIG. 1 is a schematic view of a feeding and dewatering arrangement for partly hydrolyzed material according to an embodiment of the present invention;

FIG. 2 is a schematic view of a system for a two-stage hydrolysis according to an embodiment of the present invention;

DETAILED DESCRIPTION OF PREFERRED EMBODIMENTS

Figure 3:
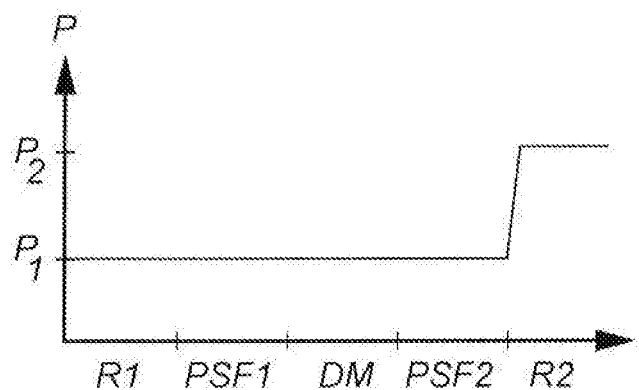
FIG. 3 is a schematic diagram of the pressure at different units or means of an arrangement or a system according to embodiments of the present invention.

In the drawings, similar or corresponding elements are denoted by the same reference numbers.

For the purpose of this disclosure, the term longitudinal refers to the direction along which a body, part or element has its greatest extension. Further, when the term longitudinal is used in connection with the axes of screws, the longitudinal axis corresponds to the rotational axis of the screw.

With reference first to FIGS. 1 and 2, the general principles of an arrangement according to an embodiment of the present invention will be discussed. FIG. 1 schematically illustrates a general view of the arrangement 1 according to an embodiment of the present invention.

In FIG. 1, the present invention is implemented in a two-stage hydrolysis system for hydrolysing lignocellulosic material. The lignocellulosic material may comprise, for example, wood-based raw materials such as wood chips, sawdust, chipped or hammer-milled forest residuals, agricultural residues such as bagasse, sugar cane straw, wheat straw, corn stover, corn cobs, and oil palm fruit residuals (so-called empty fruit bunches). Other types of lignocellulosic material include grasses, reeds and energy canes. Preferably, the lignocellulosic material entering the process has a particle size or thickness of up to 6 mm.

The arrangement for feeding and dewatering partly hydrolyzed biomass material is arranged to receive the partly hydrolyzed biomass material at a first pressure $P_1$ and deliver the dewatered biomass material further in system where the biomass material is treated at a higher pressure $P_2$. For example, as will be described below with respect to FIG. 2, the arrangement may be arranged between a first reactor unit 10 operating at a pressure of $P_1$ and a second reactor unit 12 operating at a pressure of $P_2$, where the second pressure $P_2$ is higher than the first pressure $P_1$. The first reactor unit 10 may be arranged to operate in a temperature range between 140-220° C., preferably above 180° C. with a treatment time in a range between 30 seconds to 20 minutes, preferably below 5 minutes. Further, the first reactor unit 10 is arranged to operate at a pressure within a range of 5-20 bar, preferably more than 10 bar, and more preferably within a range of 13-16 bar. The second reactor unit may be arranged to operate in at a temperature above 180° C., preferably between 180-300° C., more preferably at a temperature range between 225-300° C., and more preferably above 235° C. with a treatment time in a range between 10 seconds and 10 minutes, preferably below 1 minute. Further, the second reactor unit 12 is arranged to operate at a pressure within a range of 25-50 bar, preferably at least 30 bar, and more preferably within a range of 35-45 bar.

In preferred embodiments of the present invention, the pressure throughout the arrangement is at least 13 bar. Further, in preferred embodiments of the present invention, the pressure increase, i.e. the pressure difference between $P_2$ and $P_1$ is at least 20 bar. A first plug screw feeder 14 is coupled to receive partly hydrolyzed material and the first plug screw feeder 14 is arranged to compress, dewater and transport the material at least at a maintained pressure $P_1$. Hence, the pressure $P_{PSF1}$ of the first plug screw feeder 14 is at least at the same level as the pressure $P_1$ of the first reactor unit 10.

The first plug screw feeder 14 comprises an outlet 21 for removal of filtrate.

According to specific embodiments of the present invention, the plug screw feeder 14 drains the material. The filtrate from the screw feeder, which contains hemicellulose sugars, may be sent to a heat exchanger (not shown) before being collected for further processing.

The arrangement 1 further comprises a dilution means 16 coupled to receive material from the first plug screw feeder 14. The dilution means 16 includes a liquid inlet 17 for receiving wash liquid, wherein the dilution means is arranged to maintain or increase the pressure. In embodiments, the dilution means 16 is a dilution screw, a mixing screw or a pump.

A second plug screw feeder 18 is coupled to receive the material and is arranged to compress, dewater and transport the material further to a stage where the operational pressure is $P_2$.

The second screw feeder 18 is arranged to operate at increased pressure, i.e. at a higher pressure the pressure $P_{DM}$ of the dilution means 16.

The second plug screw feeder 18 comprises an outlet 22 for removal of filtrate. According to specific embodiments of the present invention, the plug screw feeder 18 drains the material. The filtrate from the screw feeder, which contains hemicellulose sugars, may be sent to a heat exchanger (not shown) before being collected for further processing.

The first plug screw feeder 14, the dilution means 16 and the second plug screw feeder 18 together achieve washing of the partly hydrolyzed lignocellulosic material. Accordingly, there is no need of additional washing apparatus, such as a conventional filter washer, wash press or drum displacement washer, between the reactors.

Figure 6:
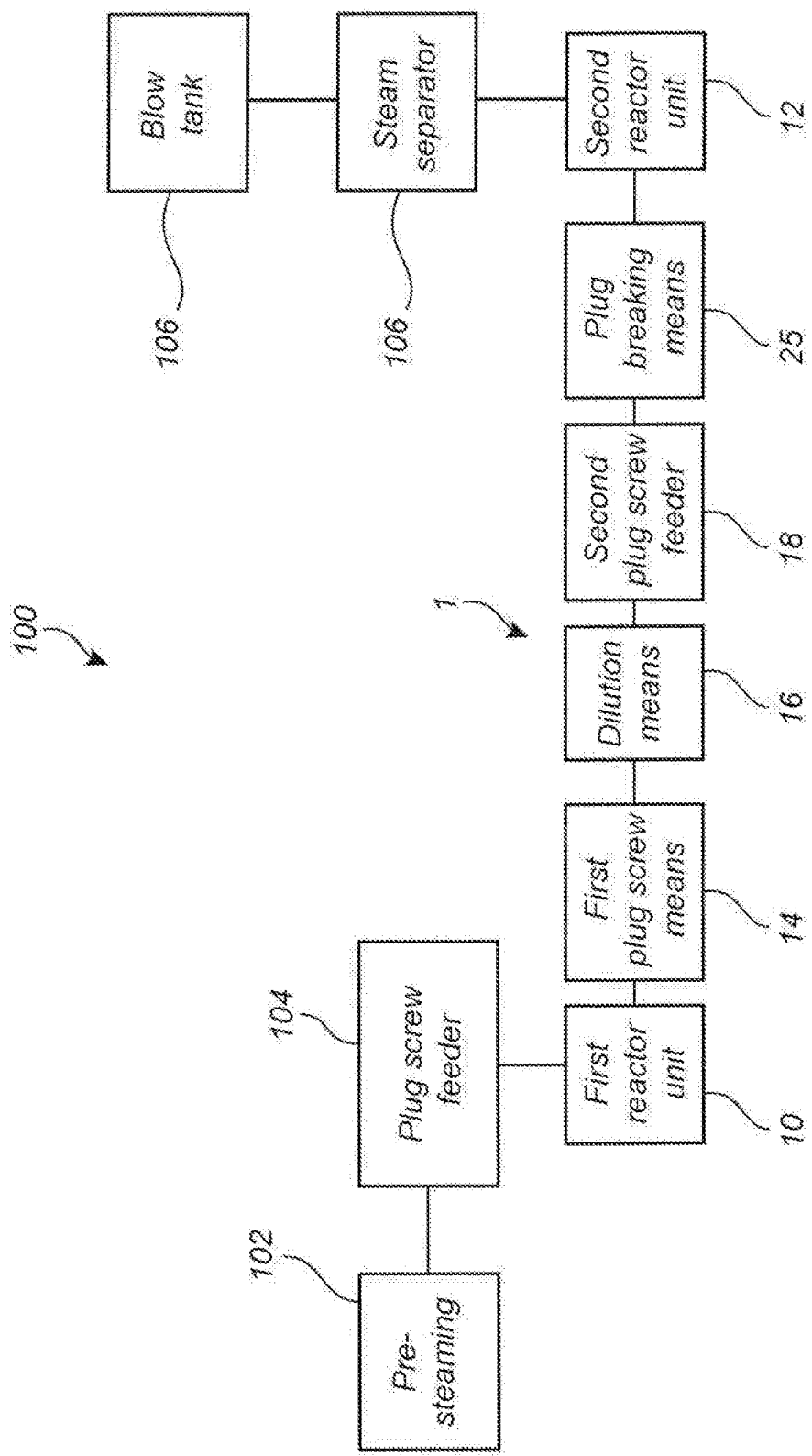
FIG. 6 is a schematic view of a system for treatment of lignocellulosic material in a hydrolysis process in which the arrangement and system of the present invention can be implemented.

According to embodiments of the system, a plug breaking means 25 is arranged to break up the material, for example, downstream the first plug screw feeder 18 (FIG. 6). In a preferred embodiment, a plug breaking means 25 is coupled between the second plug screw feeder 18 and the second reactor unit 12. Thereby, it is possible to operate the second reactor unit 12 at high temperatures and with short treatment times since the biomass material entering the second reactor unit may have smaller particle sizes than the biomass material entering the process and the first reactor unit. According to embodiments of the present invention, the plug breaking means comprises a rotatable plug breaking member such as rotating disc.

Hence, according to the general principles of the present invention, the arrangement comprises a first transport unit where material is received at a first pressure and is transported, dewatered and compressed and the pressure is maintained or increased in at least one plug screw feeder. Thereafter, dilution means is arranged where washing liquid is added and the pressure is maintained or increased, but preferably increased. A second transport unit is arranged to receive diluted material where material is transported, dewatered and compressed and the pressure is maintained or increased in at least one plug screw feeder before the material is fed further to a stage where the operational pressure is higher than the pressure on the receiving end.

Figure 7:
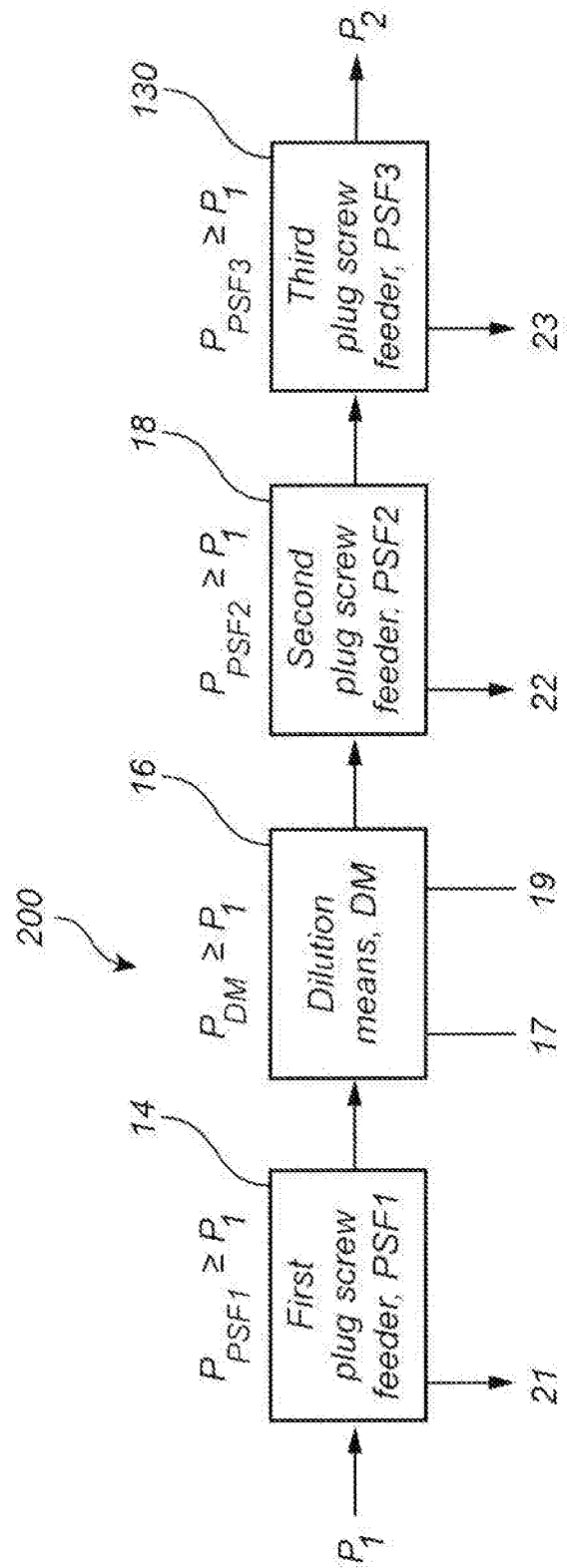
FIG. 7 is a schematic view of a feeding and dewatering arrangement for partly hydrolyzed material according to another embodiment of the present invention.

It should be stressed that the arrangement according to the present invention may include more than two plug screw feeders. For example, the first transport unit may include more than one plug screw feeder and the second transport unit may include more than one plug screw feeder. An example of another embodiment of the arrangement is shown in FIG. 7.

The screws of the plug screw feeders are arranged to rotate at a variable speed. The rotational speed of the screws determines the rate of material flow. If the production flow is to be increased, the rotational speed of the screw has to be increased to maintain the same density in the plug screw feeder. If the rotational speed of the plug screw is maintained while the production flow increases, the density will increase. By increasing the material density in the plug screw feeder an essentially gas- and fluid-tight plug of the lignocellulosic material is created towards the end of the plug screw feeder.

Turning now to FIG. 2, a two-stage system for hydrolysis of biomass material according to the present invention will be discussed. According to embodiments of the system, the incoming biomass material has a high solid content of at least 30% and preferably more than 50%, e.g., 50-85%.

The system for two-stage hydrolysis includes a first reactor unit 10 operated at a first pressure $P_1$ and a second reactor unit 12 operated at a second pressure $P_2$. The second pressure $P_2$ is higher than the first pressure $P_1$, for example, the first reactor 10 may be run at a pressure of about 13-16 bar and the second reactor 12 is run at a pressure of about 35-45 bar.

The first reactor 10 may be a horizontal reactor, a vertical reactor or an inclined reactor. In this embodiment, the reactor is horizontal and the biomass material is moved towards a discharge end in the longitudinal direction using, for example, a conveyor screw. The screw speed is adjustable to make it possible to vary a retention time or production rate through the reactor. The first reactor unit 10 comprises an inlet 24 for addition of steam. Further, acids such as sulfuric acid, phosphoric acid, hydrochloric acid, acetic acid or other acids can be added to the process.

The first reactor unit 10 is arranged to operate in a temperature range between 140-220° C., preferably above 180° C. with a treatment time in a range between 30 seconds to 20 minutes, preferably below 5 minutes. Further, first reactor unit 10 is arranged to operate at a pressure within a range of 5-20 bar, preferably more than 10 bar, and more preferably within a range of 13-16 bar.

The second reactor 12 may be a horizontal reactor, a vertical reactor or an inclined reactor. In this embodiment, the reactor is horizontal and the biomass material is moved towards a discharge end in the longitudinal direction using, for example, a conveyor screw. The screw speed is adjustable to make it possible to vary a retention time or production rate through the reactor. A mixing element may be arranged to break up the material and mix it with steam. The second reactor unit 12 comprises an inlet 26 for addition of steam. Further, acids such as sulfuric acid, phosphoric acid, hydrochloric acid, acetic acid or other acids can be added to the process.

The second reactor unit is arranged to operate in at a temperature above 180° C., preferably between 180-300° C., more preferably at a temperature range between 225-300° C., and more preferably above 235° C. with a treatment time in a range between 10 seconds and 10 minutes, preferably below 1 minute. Further, the second reactor unit 12 is arranged to operate at a pressure within a range of 25-50 bar, preferably at least 30 bar, and more preferably within a range of 35-45 bar.

The system 20 according to this embodiment includes an arrangement 1 according to FIG. 1 described above and hence a first plug screw feeder 14 is coupled to the first reactor unit 10 to receive partly hydrolyzed material. The first plug screw feeder is arranged to compress and transport the material at least at a maintained pressure $P_1$.

According to specific embodiments of the present invention, the plug screw feeder 14 drains the material and the filtrate from the screw feeder may be sent to a heat exchanger (not shown) before being collected for further processing.

The system 20 further comprises a dilution means 16 coupled to receive material from the first plug screw feeder 14. The dilution means 16 includes a liquid inlet 17 for receiving liquid to wash the material, wherein the dilution means 16 is arranged to maintain or increase the pressure. A second plug screw feeder 18 coupled to receive the diluted material and is arranged to compress and transport the material to the second reactor unit 12. The second screw feeder 18 is arranged to operate at a maintained or increased pressure, i.e. at the pressure of the dilution means 16 or at a higher pressure.

According to embodiments of the system, a plug breaking means 25 is coupled between the first and second reactor units, 10 and 12 (see FIG. 6). In a preferred embodiment, the plug breaking means 25 is coupled between the second plug screw feeder 14 and the second reactor unit 12 to break-up the plug and disintegrate the biomass material before entering the second reactor unit 12. Thereby, it is possible to operate the second reactor unit 12 at high temperatures and with a short treatment times. According to embodiments of the present invention, the plug breaking means comprises a rotatable plug breaking member such as rotating disc.

In FIG. 3, a diagram illustrating the pressure in the units or means of an arrangement or a system according to embodiments of the present invention is shown. As can be seen, the operating pressure in the first reactor unit 10 is $P_1$, the pressure is maintained during the transport in the first plug screw feeder 14 and in the dilution means 16. The pressure is then increased to $P_2$ at entrance to the second reactor unit 12 from the second plug screw feeder 18. It should however be stressed that this pressure curve is exemplary and that other embodiments of the system according to the present invention may disclose other pressure curves as illustrated in FIGS. 4 and 5.

Figure 4:
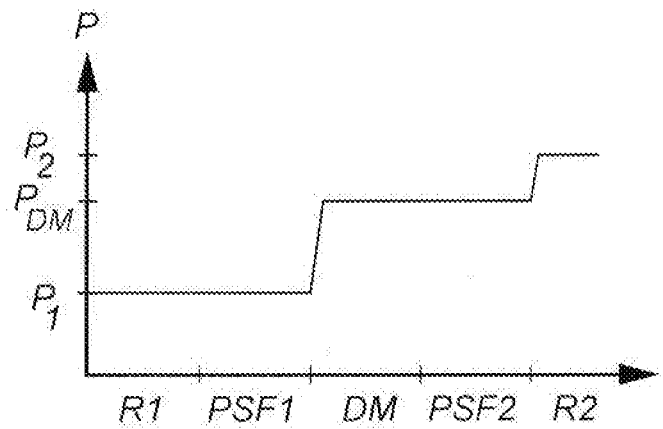
FIG. 4 is a schematic diagram of the pressure at different units or means of an arrangement or a system according to other embodiments of the present invention.

In FIG. 4, a diagram illustrating the pressure in the units or means of an arrangement or a system according to embodiments of the present invention is shown. As can be seen, the operating pressure in the first reactor unit 10 is $P_1$, the pressure is maintained in the first plug screw feeder 14 and is increased in or at the entrance to the dilution means 16 from $P_1$ to $P_{DM}$. The pressure is then increased further to $P_2$ at entrance to the second reactor unit 12 from the second plug screw feeder 18.

Figure 5:
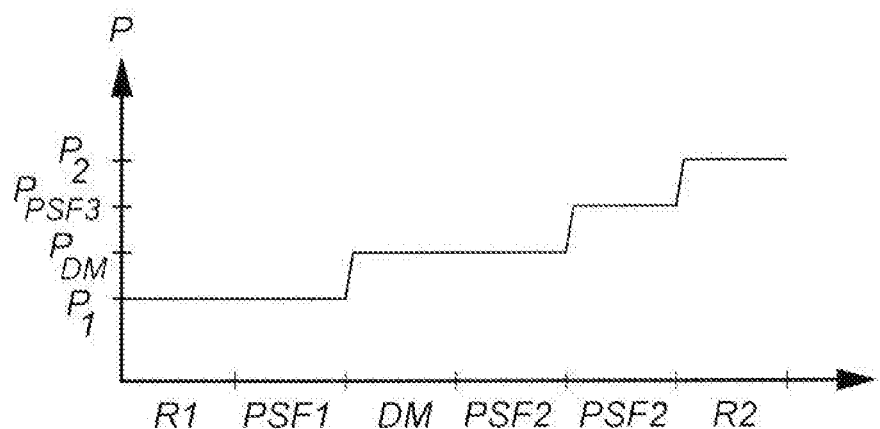
FIG. 5 is a schematic diagram of the pressure at different units or means of an arrangement or a system according to further embodiments of the present invention.

In FIG. 5, a diagram illustrating the pressure in the units or means of an arrangement or a system according to embodiments of the present invention is shown. This embodiment is described in more detail below with reference to FIG. 7. As can be seen in FIG. 5, the operating pressure in the first reactor unit 10 is $P_1$, the pressure is increased in the dilution means 16 to $P_{DM}$ and is increased further in the third plug screw feeder 130 from $P_{DM}$ to $P_{PSF3}$. The pressure is maintained at $P_{PSF3}$ during transport in the third plug screw feeder 130 and is finally increased to $P_2$ at the entrance to the second reactor unit 12.

According to an embodiment, the operating pressure in the first reactor unit 10 is $P_1$, the pressure ($P_{SF1}$) is increased in the first plug screw feeder 14. In the dilution means 16 the pressure ($P_{DM}$) is increased or maintained and is increased further in the second plug screw feeder 18 from $P_{PSF1}$ or $P_{DM}$ to $P_{PSF2}$ which equals to the pressure $P_2$ of the second reactor unit 12.

With reference now to FIG. 6, a system 100 for treatment of lignocellulosic material in a hydrolysis process in which the present invention can be implemented will be described. In this exemplary system, a pre-steaming is the first stage and the final stage is a slurry of fully hydrolyzed biomass. Thus, the biomass material is received in the system in a pre-steaming stage 102. The pre-steaming vessel acts as a buffer for the biomass, providing, for example, a retention time of 10 minutes.

After the pre-steaming vessel follows a feeding unit such as a plug screw feeder 104. As the biomass is moved forward through the plug screw feeder 104, the biomass is compressed and dewatered. The compressed material forms a solid plug acting as a pressure seal.

The biomass material is then fed to a system for two-stage hydrolysis according to the present invention, i.e. the biomass material is fed to a first reactor unit 10.

After the first reactor unit 10, the biomass material is fed further to an arrangement 1 according to the present invention, i.e., the biomass material is fed to a first plug screw feeder 14 for compression and dewatering.

A plug breaking means 25 may be coupled between the first and second reactor units 10, 12. In a preferred embodiment, the plug breaking means 25 is coupled between the second plug screw feeder 18 and second reactor unit 12 to break up the plug and provide a pressure seal in case the plug is lost. By breaking up the material, the material will have smaller particle size when entering the second reactor unit 12 and, thereby, it is possible operate the second reactor unit 12 at high temperatures and with short treatment times. It is also possible to add steam and/or acid to the biomass.

A dilution vessel 16 is arranged to receive the compressed and dewatered biomass material. In embodiments of the present invention, the pressure is increased in the dilution vessel 16 before the biomass material is sent to the second plug screw feeder 18. The dilution vessel is arranged to mix dilution water and steam with biomass material. Dilution water is added to further wash and remove hemicelluloses sugars from the biomass by dewatering/draining prior to treatment in the second reactor unit 12. It is also possible to add steam and/or acid to the biomass in the dilution means 16.

In the second plug screw feeder 18, which is pressurized, the biomass material is dewatered and compressed before being fed to the second reactor unit 12. Preferably, the filtrate from both the first and second plug screw feeders, 14 and 18, which is rich in hemicellulose sugars, is provided to a heat exchanger (not shown) before being collected for further processing.

After the second reactor unit 12, the processed biomass material is sent to a steam separator 106. The steam separator 106 may be a cyclone where the steam and biomass material, or hydrolysis slurry, from the second reactor unit 12 enters the vessel tangentially along the wall. The biomass material falls along the wall towards the bottom and steam is separated by flashing and moves upwards. The pressure of the vessel is controlled with a control valve on the steam outlet. The separated material is discharged through the bottom via a blow valve. The steam may be recovered and used in the pre-steaming stage 102. In an embodiment, the steam separator comprises a vessel including a separation part or section arranged with at least one inlet for receiving biomass material mixed with steam and at least one control outlet for discharging the steam. The incoming stream of biomass and steam enters the separation section tangentially at the top. The pressure cyclone may operate at a pressure of 3-50 bar and at a temperature of 130-265° C. A biomass collection section is arranged to be filled at least partly with liquid during operation and is arranged to receive the biomass material after separation from steam. The biomass collection section is arranged at a lower part of the housing and preferably below the separation section. The liquid level acts as a pressure lock between the vessel and the discharge which enables pressurization of the vessel.

An agitator is used for mixing the biomass material into the liquid. At least one control valve and/or a liquid addition control valve can be used to control the level of the liquid in the biomass collection section to obtain the pressure lock. The valves together with a steam control valve co-operate to obtain an adjustable steam pressure within the steam separation section.

After dilution the biomass material output from the steam separator 106 is collected in a blow tank 108 acting as a buffer between the reactor part of the process and the following separation and washing stages. The solid residual, which contains mainly lignin, can, for example, be sent to further refining or used to produce fuel pellets.

In FIG. 7, the present invention is implemented in a two-stage hydrolysis system where the arrangement for feeding and dewatering partly hydrolyzed biomass material is arranged to receive the partly hydrolyzed biomass material at a first pressure $P_1$ and deliver the dewatered biomass material further in the system where the biomass material is treated at a higher pressure $P_2$. For example, as described with respect to FIG. 2, the arrangement may be arranged between a first reactor unit 10 operating at a pressure of $P_1$ and a second reactor unit 12 operating at a pressure of $P_2$, where the second pressure $P_2$ is higher than the first pressure $P_1$, for example, the first reactor 10 is run at a pressure of about 13-16 bar and the second reactor 12 is run at a pressure of about 35-45 bar.

A first plug screw feeder 14 is coupled to receive partly hydrolyzed material and the first plug screw feeder 14 is arranged to compress, dewater and transport the material at least at a maintained pressure $P_1$. Hence, the pressure $P_{PSF1}$ of the first plug screw feeder 14 is at least at the same level as the pressure $P_1$ of the first reactor unit 10.

According to specific embodiments of the present invention, the plug screw feeder 14 drains the material and the filtrate from the screw feeder may be sent to a heat exchanger (not shown) before being collected for further processing.

The arrangement 1 further comprises a dilution means 16 coupled to receive material from the first plug screw feeder 14. The dilution means 16 includes a liquid inlet 17 for receiving liquid to wash the material, wherein the dilution means is arranged to maintain or increase the pressure. In embodiments, the dilution means 16 is a dilution screw.

A second plug screw feeder 18 is coupled to receive the diluted material and is arranged to compress, dewater and transport the material further to a third plug screw feeder 130. The third plug screw feeder 130 is arranged to compress, dewater and transport the material further to a stage where the operational pressure is $P_2$. The second plug screw feeder 18 is arranged to operate at a maintained or increased pressure, i.e. at the pressure $P_{DM}$ of the dilution means 16 or at a higher pressure. The pressure $P_{PSF2}$ of the second plug screw feeder 18 is thus at least at the same level as the pressure $P_{DM}$ of the dilution means 16. The third plug screw feeder 130 is arranged to operate at a maintained or increased pressure, i.e., at the pressure $P_{PSF2}$ of the second plug screw feeder 18 or at a higher pressure. The pressure $P_{PSF3}$ of the third plug screw feeder 130 is thus at least at the same level as the pressure $P_{PSF2}$ of the second plug screw feeder 18.

With more than two plug screw feeders between the reactors, like in FIG. 7, for example, an even better washing and an even larger pressure increase between the first and the second reactors can be accomplished.

Figure 9:
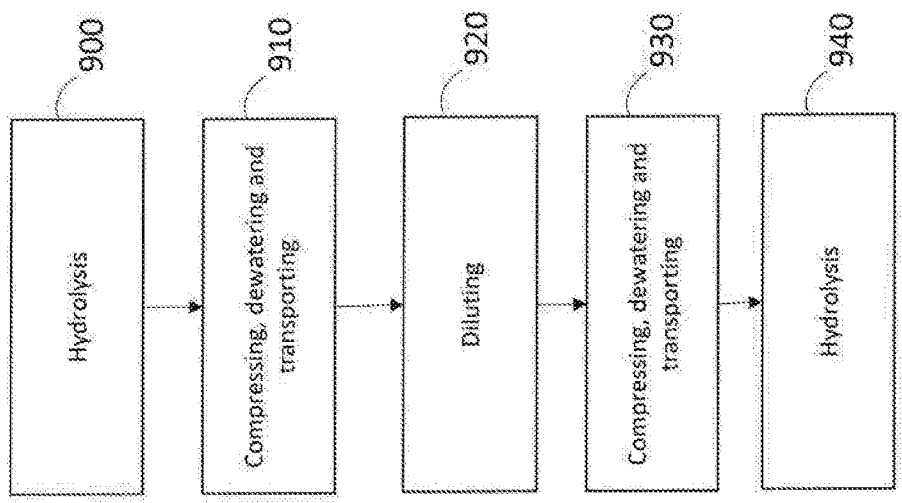
FIG. 9 is a schematic view of a method according to a further embodiment of the present invention
Figure 8:
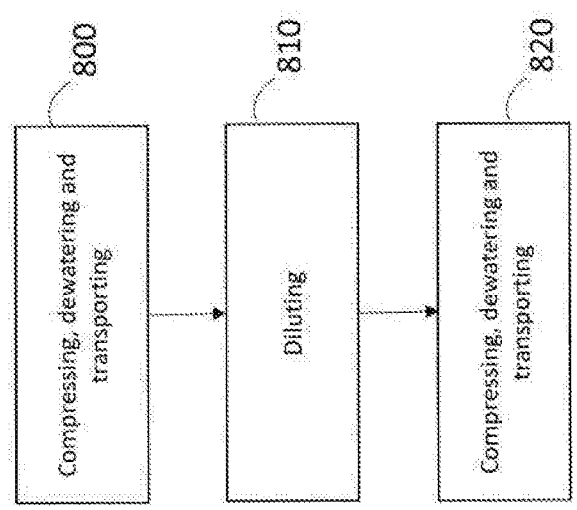
FIG. 8 is a schematic view of a method according to the present invention.

With reference to FIG. 8, a method for feeding and washing lignocellulosic material in a hydrolysis process between a first reactor unit 10 where the material is partly hydrolyzed and a second reactor unit 12 where the material is further hydrolyzed, wherein the first reactor unit 10 operates at a first pressure $P_1$ and the second reactor unit 12 operates at a second pressure $P_2$ being higher than the first pressure $P_1$ will be described. The method comprises compressing, dewatering and transporting 800 the partly hydrolyzed material at a pressure $P_{PSF1}$ being higher than the first pressure $P_1$; diluting 810 the material and receiving liquid to wash the material at maintained or increased pressure $P_{DM}$; and compressing, dewatering and transporting 820 the material to further processing at a pressure $P_{PSF2}$ being higher than the pressure $P_{PSF1}$ of the first compressing, dewatering and transporting step. In another embodiment of the method, see FIG. 9, a lignocellulosic material is partly hydrolyzed a first hydrolysis 900 and the partly hydrolyzed material is further hydrolyzed in a second hydrolysis 940, wherein the first hydrolysis is operated at a first pressure $P_1$ and the second hydrolysis operates at a second pressure $P_2$ being higher than the first pressure $P_1$. The material partly hydrolyzed in the first hydrolysis is compresses, dewatered and transported 910 at a pressure $P_{PSF1}$ being higher than the first pressure $P_1$. The method further comprises diluting 920 the material and receiving liquid to wash the material, wherein the dilution is operated at maintained or increased pressure $P_{DM}$; and compressing, dewatering and transporting 930 the diluted material to the second hydrolysis 940 at a pressure $P_{PSF2}$ being higher than the pressure $P_{PSF1}$ of the compressing, dewatering and transporting step. The pressure at the second compressing, dewatering and transporting step 930 is preferably increased to the pressure $P_2$ of the second hydrolysis.

The invention shall not be considered limited to the embodiments illustrated, but can be modified and altered in many ways by one skilled in the art, without departing from the scope of the appended claims.

The invention claimed is:

1. An arrangement for feeding and washing lignocellulosic material in a hydrolysis process between a first reactor unit where the material is partly hydrolyzed and a second reactor unit where the material is further hydrolyzed, wherein the first reactor unit operates at a first pressure and the second reactor unit operates at a second pressure being higher than the first pressure, said arrangement comprising:
   a first plug screw feeder arranged to receive the partly hydrolyzed material from the first reactor unit and being arranged to compress and dewater the partly hydrolyzed material, and transport the material compressed and dewatered in the first plug screw feeder, wherein the first plug screw feeder is arranged to operate at a pressure being higher than the first pressure;
   a dilution vessel coupled to receive the material processed from the first plug screw feeder and including a liquid inlet for receiving liquid to wash the material processed from the first plug screw feeder, wherein the dilution vessel is arranged to maintain or increase the pressure; and
   a second plug screw feeder arranged to receive the material processed from the dilution vessel and being arranged to compress and dewater the material processed from the dilution vessel, and transport the material compressed and dewatered in the second plug screw feeder to further processing, wherein the second plug screw feeder is arranged to operate at a pressure being higher than the pressure of the first plug screw feeder.

2. The arrangement according to claim 1, wherein the dilution vessel is arranged to increase the pressure from the pressure of the first plug screw feeder.

3. The arrangement according to claim 1, wherein the dilution vessel includes an inlet for receiving steam, wherein the material processed from the first plug screw feeder is mixed with steam and liquid.

4. The arrangement according to claim 1, wherein the second plug screw feeder is arranged to operate at a pressure of at least the pressure of the dilution vessel.

5. The arrangement according to claim 1, wherein the dilution vessel is arranged to increase the pressure to the second pressure.

6. The arrangement according to claim 1, wherein a third plug screw feeder is arranged to compress and dewater the material processed from the second plug screw feeder, and transport the material compressed and dewatered in the third plug screw feeder further, wherein the third screw feeder is arranged to operate at a pressure being higher than the pressure of the second plug screw feeder.

7. The arrangement according to claim 1, wherein a plug breaker is coupled to the second plug screw feeder.

8. The arrangement according to claim 7, wherein the plug breaker comprises a rotatable plug breaking member.

9. The arrangement according to claim 1, wherein the lignocellulosic material has a solid content of at least 30%.

10. A system for two-stage hydrolysis comprising:
    a first reactor unit where a lignocellulosic material is partly hydrolyzed and a second reactor unit for further hydrolysis of the partly hydrolyzed material, wherein the first reactor unit operates at a first pressure and the second reactor unit operates at a second pressure being higher than the first pressure;
    a first plug screw feeder coupled to the first reactor unit arranged to receive the partly hydrolyzed material from the first reactor unit and being arranged to compress and dewater the partly hydrolyzed material, and transport the material compressed and dewatered in the first plug screw feeder, wherein the first plug screw feeder is arranged to operate at a pressure being higher than the first pressure;
    a dilution vessel coupled to receive the material processed from the first plug screw feeder and including a liquid inlet for receiving liquid to wash the material processed from the first plug screw feeder, wherein the dilution vessel is arranged to maintain or increase the pressure; and
    a second plug screw feeder arranged to receive the material processed from the dilution vessel and being arranged to compress and dewater the material processed from the dilution vessel, and transport the material compressed and dewatered in the second plug screw feeder to the second reactor unit, wherein the second plug screw feeder is arranged to operate at a pressure being higher than the pressure of the first plug screw feeder.

11. The system according to claim 10, wherein the dilution vessel is arranged to increase the pressure from the pressure of the first screw feeder.

12. The system according to claim 10, wherein the dilution vessel includes an inlet for receiving steam, wherein the material processed from the first plug screw feeder is mixed with steam and liquid.

13. The system according to claim 10, wherein the second plug screw feeder is arranged to operate at a pressure of at least the pressure of the dilution vessel.

14. The system according to claim 10, wherein the dilution vessel is arranged to increase the pressure to the second pressure.

15. The system according to claim 10, wherein the first plug screw feeder is directly coupled to the first reactor unit to receive the partly hydrolyzed material and is arranged to compress the partly hydrolyzed material, and transport the material compressed in the first plug screw feeder to the dilution vessel; and the second plug screw feeder is directly coupled to the dilution vessel and is arranged to compress and transport the material processed from the dilution vessel to the second reactor unit.

16. The system according to claim 10, wherein the first reactor unit is arranged to operate at a temperature above 180° C. degrees.

17. The system according to claim 10, wherein the second reactor unit is arranged to operate at a temperature above 235° C. degrees.

18. The system according to claim 10, wherein the first reactor unit is arranged to operate with a treatment time below 5 minutes.

19. The system according to claim 10, wherein the second reactor unit is arranged to operate with a treatment time below 1 minute.

20. The system according to claim 10, wherein the first reactor unit includes a horizontal, or vertical, or inclined reactor.

21. The system according to claim 10, wherein the second reactor unit includes a horizontal, or vertical, or inclined reactor.

22. The system according to claim 10, wherein the first and second reactors each comprise a conveyor screw with an adjustable rotational speed for transporting the material processed from the first and second reactors towards a discharge outlet at a desired rate.

23. The system according to claim 10, wherein a plug breaker is coupled between the second plug screw feeder and the second reactor unit.

24. The system according to claim 23, wherein the plug breaker comprises a rotatable plug breaking member.

25. The system according to claim 10, wherein the lignocellulosic material has a solid content of at least 30%.

26. A method for feeding and washing lignocellulosic material in a hydrolysis process between a first reactor unit where the material is partly hydrolyzed and a second reactor unit where the material is further hydrolyzed, wherein the first reactor unit operates at a first pressure and the second reactor unit operates at a second pressure being higher than the first pressure, the method comprising the steps of:

a) compressing and dewatering the partly hydrolyzed material, and transporting the material compressed and dewatered in the step a) at a pressure being higher than the first pressure;

b) diluting the material processed from the step a) and receiving liquid to wash the material processed from the step a) at maintained or increased pressure; and c) compressing and dewatering the material processed from the step b), and transporting the material compressed and dewatered in the step c) to further processing at a pressure being higher than the pressure in the step a).

27. A method for two-stage hydrolysis comprising:

a first hydrolysis where a lignocellulosic material is partly hydrolyzed and a second hydrolysis of the partly hydrolyzed material, wherein the first hydrolysis is operated at a first pressure and the second hydrolysis operates at a second pressure being higher than the first pressure, wherein the method further comprises the steps of;

a) compressing and dewatering the partly hydrolyzed material, and transporting the material compressed and dewatered in the step a) at a pressure being higher than the first pressure;

b) diluting the material processed from the step a) and receiving liquid to wash the material processed from the step a), wherein the dilution is operated at maintained or increased pressure; and c) compressing and dewatering the material processed from the step b), and transporting the material compressed and dewatered in the step c) to the second hydrolysis at a pressure being higher than the pressure in the step a).

* * * * *